Figure 3:
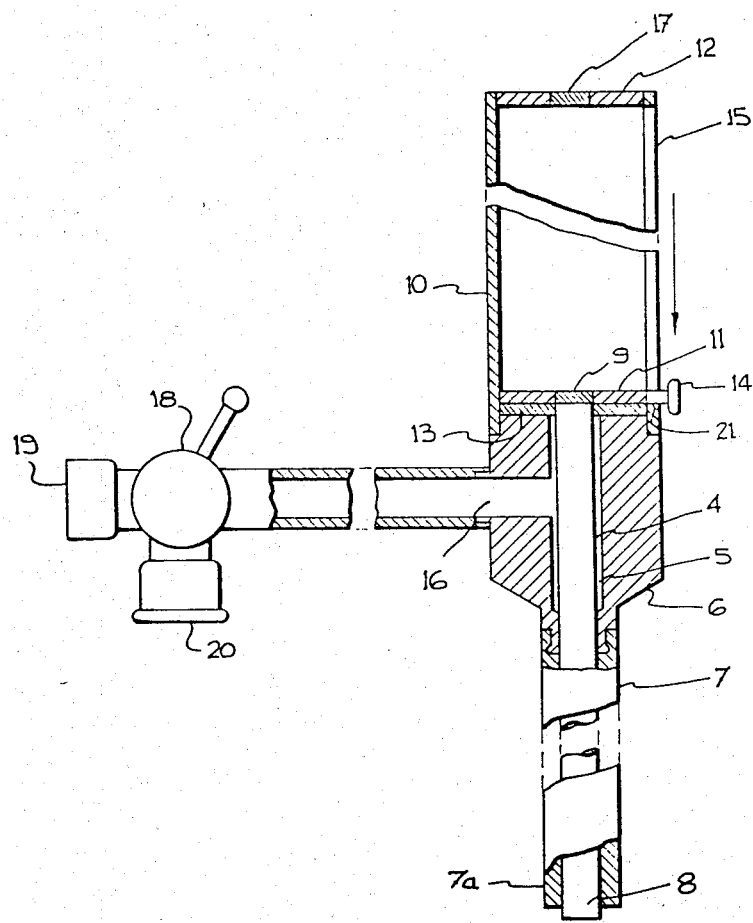

United States Patent [19]

Tchervenkov et al.

[11] Patent Number: 4,585,440
[45] Date of Patent: Apr. 29, 1986

[54] INTRAVENOUS CATHETER ASSEMBLY

[76] Inventors: Jean Tchervenkov; Christo Tchervenkov, both of 2760 Napoleon Blvd., Brossard, Canada, J4Y 2A3

[21] Appl. No.: 747,445

[22] Filed: Jun. 21, 1985

[30] Foreign Application Priority Data

Feb. 1, 1985 [CA] Canada ................................. 473403

[51] Int. Cl.⁴ .............................................. A61M 5/00
[52] U.S. Cl. .................... 604/164; 604/167; 604/168; 604/267
[58] Field of Search ................... 604/164–168, 604/267; 27/24 A

[56] References Cited

U.S. PATENT DOCUMENTS

| 3,313,299 | 4/1967 | Spademan . |
| 3,851,647 | 12/1974 | Monestere . |
| 3,977,400 | 8/1976 | Moorehead ...................... 604/16 X |
| 4,073,297 | 2/1978 | Kopp ............................. 604/167 X |
| 4,099,528 | 7/1978 | Sorenson . |
| 4,191,186 | 3/1980 | Keeler . |
| 4,224,943 | 9/1980 | Johnson . |
| 4,270,535 | 6/1981 | Bogue . |
| 4,299,217 | 11/1981 | Sagae . |
| 4,417,886 | 11/1983 | Frankhouser et al. . |
| 4,464,171 | 8/1984 | Garwin .......................... 604/164 X |

FOREIGN PATENT DOCUMENTS

| 952390 | 6/1974 | Canada . |
| 1000580 | 3/1976 | Canada . |
| 1039598 | 9/1978 | Canada . |
| 1103547 | 12/1981 | Canada . |
| 1151043 | 2/1983 | Canada . |

Primary Examiner—Stephen C. Pellegrino
Attorney, Agent, or Firm—Robic, Robic & Associates

[57] ABSTRACT

The present invention relates to an intravenous catheter assembly which is provided with a catheter plunger tube which can be used to inhibit the formation of blood clots in the catheter when the catheter is not in use.

2 Claims, 4 Drawing Figures

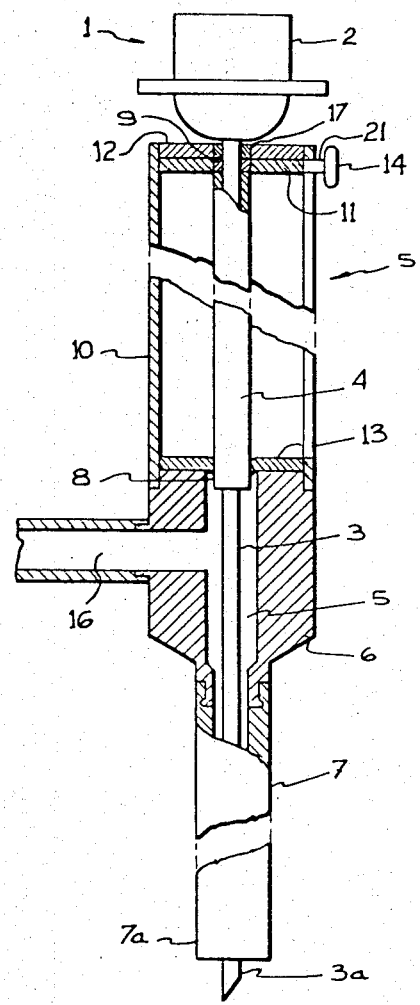
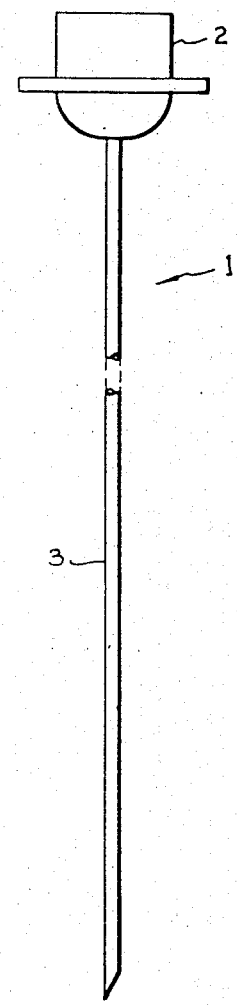
FIG. 1
FIG. 2

INTRAVENOUS CATHETER ASSEMBLY

The present invention relates to an intravenous catheter which can be placed into blood vessels and when once installed facilitates the intermittent administration of fluids, drugs, etc. to patients.

In accordance with known techniques a flexible catheter is provided which is disposed about a hollow introducer needle (trocar). In order to introduce the catheter into a blood vessel the sharp tip of the needle is used to pierce the wall of a blood vessel. Thereafter, the catheter is guided over the needle into the vessel. Once the catheter is in position in the blood vessel the needle is removed, i.e. leaving the catheter tube behind. Examples of known techniques are disclosed in the following references:

(a) U.S. Pat. Nos.: 4,299,217, 4,224,943, 3,313,299, 4,417,886, 4,191,186, 3,851,647, 4,270,535, 4,099,528, 4,073,297, 4,261,357, 4,000,739, 3,853,127, 4,338,934, 4,314,555, and (b) Canadian Pat. Nos.: 1,151,043, 1,103,547, 1,039,598, 1,000,580, 952,390.

It would be advantageous to have a catheter of the type described above wherein the clotting of blood adjacent the distal end (i.e. tip) of the catheter can be inhibited.

The present invention relates to an intravenous catheter assembly which is provided with a catheter plunger tube which can be used to inhibit the formation of blood clots in the catheter when the catheter is not in use.

The present invention, in particular, provides an intravenous catheter assembly comprising:

(i) a hub having a central bore disposed therethrough,
(ii) a flexible catheter tube of elastic material, one end of said tube being secured to the hub at one end of said bore, said catheter tube being aligned axially with said bore,
(iii) sealing means mounted at the other end of said bore,
(iv) a passage angularly disposed relative to said bore, said passage being disposed intermediate the ends of the bore and being in fluid communication therewith,
(v) a catheter plunger tube of rigid or semi-rigid material having a blunt end, said sealing means slidingly engaging the outer surface of said plunger tube to prevent the flow of fluid,
(vi) a resealable plug mounted at the other end of said plunger tube,
(vii) means for supporting said plunger tube coaxially relative to said bore, said plunger tube being displaceable between a retracted position and an extended position,
(viii) means for urging said plunger tube between said positions,
(ix) a removable trocar consisting of a fluid collecting chamber and a hollow introducer needle for introducing said catheter tube into a blood vessel, said needle being in fluid communication with said chamber, and wherein (a) said needle extends through said plunger tube, said bore and said catheter tube, the sharpened end of said needle projecting beyond the distal end of said catheter tube and said resealable plug slidingly engaging the outer surface of said needle to permit sealing of said plunger tube when said needle is withdrawn therefrom, (b) said plunger tube and said introducer needle are relatively dimensioned so that the plunger tube slidingly engages the outer wall surface of said needle, (c) said plunger tube and said catheter tube are relatively dimensioned so that the plunger tube slidingly engages the inner wall surface of the catheter tube, and (d) said plunger tube and said catheter are relatively dimensioned in length so that when in said extended position the blunt end of said plunger tube projects slightly beyond the distal end of said catheter tube and when in said retracted position the blunt end of said plunger is intermediate said passage and said sealing means.

Figure 4:
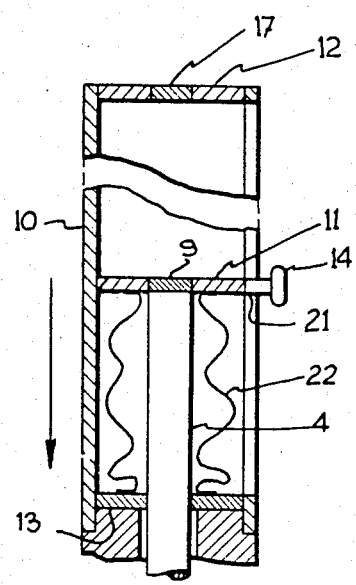

In drawings which illustrate an embodiment of the present invention:

FIG. 1 illustrates a partial cut-away view of an assembled intravenous catheter in accordance with the present invention, FIG. 2 illustrates a trocar in accordance with the present invention, FIG. 3 illustrates an intravenous catheter in accordance with the present invention with the trocar removed, and FIG. 4 illustrates a collapsable protective sheath surrounding the plunger.

With respect to each of the figures the same reference numerals are used when referring to the same elements.

The assembled intravenous catheter illustrated in FIG. 1 includes a removable trocar 1 which as can be seen in FIG. 2 consists of an upper fluid (i.e. blood) collecting chamber 2 and a lower hollow introducer needle 3. The chamber 2 and the needle 3 are in fluid communication so that when, the needle pierces the wall of a blood vessel, blood will pass up thru the needle 3 and collect in the chamber 2 to confirm that the needle has pierced the wall of the blood vessel. The trocar can be made of any suitable rigid material e.g. a metal such as stainless steel. The trocar can, for example, be from 113 to 118 mm. long, the needle itself varying, for example, in length from 88 to 93 mm.

Turning back to FIG. 1, the needle 3 extends through the catheter plunger tube 4, the central bore 5 of hub 6 and the catheter tube 7. As can be seen the catheter tube 7 and the needle 3 are relatively dimensioned in length so that a tip portion 3a of the needle 3 extends beyond the distal end 7a of the catheter tube 7.

The plunger tube 4 has a blunt end 8 and is provided at the other end thereof with a resealable plug 9. The resealable plug 9 slidingly engages the outer surface of the needle 3 to permit sealing of the plunger tube once the needle is withdrawn from the assembly.

In the embodiment illustrated in FIGS. 1 and 3 the assembly is provided with a support structure for said plunger tube 4 to axially support the tube 4 relative to the bore 5, i.e. coaxially. The support structure comprises a cylindrical tubular wall 10 and a circular end cap member 11, disposed therein. The cap member 11 is dimensioned relative to the wall 10 so as to slidingly engage the inner surface of the wall 10. The tubular wall 10 is closed off at one end by cap member 12 and at the other end by a sealing means 13 which can for example be made of a flexible silicon rubber membrane. The sealing means 13, which is fixed to the hub 6, slidingly engages the outer surface of the plunger tube 4 to prevent the flow of fluid from the bore 5, i.e. to provide a fluid tight seal around the plunger tube 4.

As indicated above the cap member 11 is slidably disposed in the wall 10. The cap member 11 is fixed to the plunger tube 4 and it includes a button-like member 14 which extends outside of the wall 10 through a longitudinal slot in wall 10 indicated generally at 15. The slot 15 extends from cap member 12 to the sealing means 13. The button-like member 14 can be used to urge the plunger tube 4 between a retracted position and an extended position.

In FIG. 1 the plunger tube 4 is shown in the retracted position. In this position the blunt end 8 of the plunger tube 4 is intermediate the angular passageway 16 and the sealing means 13.

In FIG. 3 the plunger tube 4 is shown in the extended position, the plunger tube 4 and the catheter tube 7 being dimensioned relatively in length so that the blunt end 8 of the plunger tube 4 projects slightly beyond the distal end 7a of the catheter tube 7.

The cap member 12 as in the case of the end cap member 11 is provided with a resealable plug 17.

The angular passageway 16 is in fliud communication with the bore 5 and the catheter tube 7 when the plunger tube 4 is in the retracted position illustrated in FIG. 1 the trocar being removed from the assembly.

The flexible catheter tube is made of an elastic material, i.e. a material which is non-allergenic, non-thrombotic e.g. teflon.

Referring to FIG. 3 the angular passageway 16 is in fluid communication with a suitable tubing which is closed off by a stop-cock 18. The purpose of the tubing etc. is to provide fluid access to a patient's circulation system, once the catheter is in place. The stop-cock shown has two infusion means. One infusion means consists of a female adapter hub 19 for receiving a correspondingly shaped male hub (not shown) for the introduction of fluid. The other infusion means consists of a resealable membrane 20, closing off an infusion chamber, for introducing fluids by means such as needles.

In order to lock the plunger tube 4 in the retracted or extended position the slot 15 may be provided at its upper and lower ends with angularly disposed side slots (not shown), for receiving the stem 21 of the button-like member 14. If the stem 21 is in the lower or upper side slot, the slot inhibits the displacement of the plunger tube 4 between the retracted and extended positions. Thus if it is desired to displace the plunger tube 4 from the retracted position (FIG. 1) to the extended position (FIG. 3) the button-like member 14 is first pushed sideways causing the cap member 11 and the attached plunger tube 4 to rotate slightly, the stem 21 being displaced from the upper side slot into slot 15. Thereafter the button-like member 14 is pushed downwardly until the plunger tube 4 is in the extended position (FIG. 3). Once in this latter position the button-like member is again pushed sideways to place the stem 21 in the lower side slot.

The plunger tube 4 is made of a rigid or semi-rigid material which can be a plastic and which like the catheter tube is non-allergenic and non thrombotic. The hub 6 can be made of a similar rigid material.

The method of inserting the catheter tube 7 into a patient's vein using the assembled catheter as illustrated in FIG. 1 is as follows:

As indicated earlier, the cap member 11 to which is fixed the plunger 4 can be urged to go up and down as the case may be between a retracted and extended position.

For insertion the cap member 11 is positioned adjacent to the cap member 12 as shown in FIG. 1, i.e. the plunger tube 4 is disposed in the retracted position. The needle tip portion 3a of the assembled catheter is brought into the viscinity of the desired blood vessel. The tip 3a is then caused to pierce the skin and thereafter the vessel. Once the vessel is pierced by the needle tip 3a, blood will collect in the blood collecting chamber 2. When this occurs, the catheter tube element 7 is caused to slide over the needle 3 and is forced into the patient's vessel. Once this operation is complete, the trocar illustrated in FIG. 2 is removed completely from the assembly; see FIG. 3.

When the catheter is being used, the plunger tube 4 is always in the upper retracted position as illustrated in FIG. 1. When the catheter is not being used but is to remain in place, a small amount of heparinized saline solution may be injected into the catheter via the stopcock 18 (see FIG. 3). Thereafter the plunger tube 4 is urged (see arrow FIG. 3) into the catheter tube 7 so that a minimal portion of the blunt end 8 of the plunger tube 4 extends just outside of the distal end 7a of the tube 7 into the vessel. The plunger 4 pushes out any fluid or blood in the catheter tube 7 back into the vessel and inhibits blood from thereafter re-entering the catheter tube 7. In this manner, the formation of clots in the catheter itself can be inhibited.

When the plunger tube 4 is in the retracted position the portion of the tube 4 within the wall 10 and intermediate the cap member 11 and the sealing means 13 may be exposed to contaminants. Thus, in accordance with an additional feature of the present invention, the exposed portion of the plunger tube 4 may be protected from contaminants when the tube 4 is not in the extended position, i.e. in order to maintain sterility during intermittent use of the attached assembly.

Referring to FIG. 4 a collapsable protective sheath 22 may, for example, be provided within the wall 10, the sheath 22 being fixed at its ends to cap member 11 and the sealing means 13. As can be seen the sheath 22 surrounds the portion of the plunger tube 4 between the cap member 11 and the sealing means 13. The sheath 22 acts to shield the tube 4 from contaminants such as bacteria when the plunger tube is in the retracted position.

In FIG. 4 the plunger tube 4 is shown as being displaced in the direction of the arrow, i.e. to the extended position. As can be seen the sheath 22 is adapted to collapse around the plunger tube 4 as the tube 4 is pushed in the direction of the arrow, the reverse occuring when the plunger tube 4 is urged into the retracted position.

The sheath 22 may be made as any suitable flexible material e.g. a rubber-like material.

The catheter assembly is maintained in sterile condition prior to use.

The embodiments of the invention in which an exclusive property or privilege is claimed are defined as follows:

1. An intravenous catheter assembly comprising
(i) a hub having a central bore disposed therethrough,
(ii) a flexible catheter tube of elastic material, one end of said tube being secured to the hub at one end of said bore, said catheter tube being aligned axially with said bore, (iii) sealing means mounted at the other end of said bore,
(iv) a passage angularly disposed relative to said bore, said passage being disposed intermediate the ends of the bore and being in fluid communication therewith,
(v) a catheter plunger tube of rigid or semi-rigid material having a blunt end, said sealing means slidingly engaging the outer surface of said plunger tube to prevent the flow of fluid,
(vi) a resealable plug mounted at the other end of said plunger tube,
(vii) means for supporting said plunger tube coaxially relative to said bore, said plunger tube being displaceable between a retracted position and an extended position,
(viii) means for urging said plunger tube between said positions,
(ix) a removable trocar consisting of a fluid collecting chamber and a hollow introducer needle for introducing said catheter tube into a blood vessel, said needle being in fluid communication with said chamber, and, wherein
(a) said needle extends through said plunger tube, said bore and said catheter tube, the sharpened end of said needle projecting beyond the distal end of said catheter tube and said resealable plug slidingly engaging the outer surface of said needle to permit sealing of said plunger tube when said needle is withdrawn therefrom,
(b) said plunger tube and said introducer needle are relatively dimensioned so that the plunger tube slidingly engages the outer wall surface of said needle,
(c) said plunger tube and said catheter tube are relatively dimensioned so that the plunger tube slidingly engages the inner wall surface of the catheter tube, and
(d) said plunger tube and said catheter are relatively dimensioned in length so that when in said extended position the blunt end of said plunger tube projects slightly beyond the distal end of said catheter tube and when in said retracted position the blunt end of said plunger is intermediate said passage and said sealing means.

2. An assembly as defined in claim 1, wherein said urging means is disposed at said other end of the plunger tube adjacent the resealable plug and wherein the portion of the plunger tube, intermediate said urging means and said sealing means mounted at the other end of said bore, is surrounded by a collapsable protective sheath for shielding said portion of the plunger tube from contaminants.

* * * * *